United States Patent
Takao

(10) Patent No.: US 10,239,997 B2
(45) Date of Patent: Mar. 26, 2019

(54) SURFACE TREATMENT AGENT FOR SUBSTRATE, COMPRISING PERFLUOROPOLYETHER GROUP-CONTAINING PHOSPHATE COMPOUND

(71) Applicant: AGC Inc., Chiyoda-ku (JP)

(72) Inventor: Kiyotaka Takao, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 15/454,564

(22) Filed: Mar. 9, 2017

(65) Prior Publication Data

US 2017/0183449 A1 Jun. 29, 2017

Related U.S. Application Data

(63) Continuation of application No. PCT/JP2015/075736, filed on Sep. 10, 2015.

(30) Foreign Application Priority Data

Sep. 17, 2014 (JP) .................................. 2014-188789

(51) Int. Cl.

| C07F 9/09 | (2006.01) |
|---|---|
| C09D 5/00 | (2006.01) |
| C08G 65/00 | (2006.01) |
| G02B 27/00 | (2006.01) |
| C08G 65/327 | (2006.01) |
| C09D 171/00 | (2006.01) |
| C10M 107/48 | (2006.01) |

(52) U.S. Cl.
CPC ............ C08G 65/327 (2013.01); C07F 9/091 (2013.01); C08G 65/007 (2013.01); C09D 5/00 (2013.01); C09D 171/00 (2013.01); C10M 107/48 (2013.01); G02B 27/0006 (2013.01); C08G 2650/48 (2013.01); C10M 2213/06 (2013.01); C10M 2213/0606 (2013.01); C10M 2225/00 (2013.01); C10M 2225/003 (2013.01); C10N 2230/04 (2013.01); C10N 2230/06 (2013.01); C10N 2230/22 (2013.01); C10N 2230/26 (2013.01); C10N 2240/06 (2013.01); C10N 2240/204 (2013.01); C10N 2240/66 (2013.01); C10N 2250/121 (2013.01); C10N 2280/00 (2013.01)

(58) Field of Classification Search
CPC .. C08G 65/327; C08G 65/007; C10M 107/48; C10M 2213/06; C10M 2213/0606; C10M 2225/00; C10M 2225/003; C10N 2230/04; C10N 2230/06; C10N 2230/22; C10N 2240/06; C10N 2240/204; C10N 2240/66; C10N 2250/121; C10N 2280/00; C07F 9/091; C09D 5/00; C09D 171/00; G02B 27/0006

See application file for complete search history.

(56) References Cited

U.S. PATENT DOCUMENTS

| 3,293,306 A | 12/1966 | Le Bleu et al. |
|---|---|---|
| 3,492,374 A | 1/1970 | Le Bleu et al. |
| 5,691,000 A | 11/1997 | Montagna et al. |
| 6,221,434 B1 * | 4/2001 | Visca .................... B82Y 30/00 427/389.8 |
| 6,653,495 B2 * | 11/2003 | Russo .................... C07F 9/091 558/114 |
| 2003/0134972 A1 | 7/2003 | Maccone et al. |
| 2004/0186216 A1 | 9/2004 | Satoh et al. |
| 2011/0189395 A1 | 8/2011 | Padigala et al. |
| 2013/0068408 A1 * | 3/2013 | Tonelli ................. C08G 65/007 162/158 |

FOREIGN PATENT DOCUMENTS

| JP | 8-3516 | 1/1996 |
|---|---|---|
| JP | 8-133928 | 5/1996 |
| JP | 11-236307 | 8/1999 |
| JP | 2000-219847 | 8/2000 |
| JP | 2003-55578 | 2/2003 |
| JP | 2003-286404 | 10/2003 |
| JP | 2006-291266 | 10/2006 |
| JP | 2008-214229 | 9/2008 |
| JP | 2011-116947 | 6/2011 |
| JP | 2011-526537 | 10/2011 |
| JP | 2012-51844 | 3/2012 |
| JP | 2012-56892 | 3/2012 |
| JP | 2012-201709 | 10/2012 |
| JP | 2013-528682 | 7/2013 |
| WO | WO 00/56694 | 9/2000 |
| WO | WO 02/077116 A1 | 10/2002 |
| WO | WO 2005/091070 A1 | 9/2005 |

(Continued)

OTHER PUBLICATIONS

International Search Report dated Dec. 22, 2015 in PCT/JP2015/075736 filed on Sep. 10, 2015.

(Continued)

Primary Examiner — James C Goloboy
(74) Attorney, Agent, or Firm — Oblon, McClelland, Maier & Neustadt, L.L.P.

(57) ABSTRACT

To provide a surface treatment agent capable of imparting excellent water/oil repellency, fingerprint stain removability, abrasion resistance and lubricity to the surface of a substrate. A surface treatment agent for a substrate, comprising a perfluoropolyether group-containing phosphate compound, a coating agent comprising the surface treatment agent and a liquid medium, and a substrate having a surface layer formed from the surface treatment agent or the coating agent.

9 Claims, No Drawings

(56) References Cited

FOREIGN PATENT DOCUMENTS

WO WO 2010/000715 A1 1/2010
WO WO 2011/151230 A1 12/2011

OTHER PUBLICATIONS

E. Hoque, et al., "Alkylperfluorosilane Self-Assembled Monolayers on Aluminum: A Comparison with Alkylphosphonate Self-Assembled Monolayers", J. Phys. Chem. C, 2007, 7 pgs.

* cited by examiner

SURFACE TREATMENT AGENT FOR SUBSTRATE, COMPRISING PERFLUOROPOLYETHER GROUP-CONTAINING PHOSPHATE COMPOUND

FIELD OF INVENTION

The present invention relates to a surface treatment agent for a substrate, comprising a perfluoropolyether group-containing phosphate compound, and a substrate having a surface layer formed from the surface treatment agent.

BACKGROUND OF INVENTION

An article having a substrate, such as an optical article, a display or an optical recording medium, is required to have properties such as water/oil repellency or stain removability so that water or fouling (such as fingerprints, sebum, sweat, cosmetics, foods, etc.) is less likely to attach on the surface, or that fouling, if has attached on the surface, can easily be removed. For example, if fouling attaches on the surface of an eyeglass lens, visibility tends to be impaired and visual quality tends to be deteriorated. If fouling attaches on the surface of an optical recording medium, a trouble is likely to be caused in recording or reproducing a signal. If fouling attaches on the surface of a display, the visibility tends to be low, and in the case of a display provided with a touch panel, the operation efficiency tends to be adversely affected.

As improvement techniques for an aluminum oxide substrate surface, a technique for forming a surface layer from a phosphate compound having a perfluoroalkyl group, such as 1H,1H,2H,2H-perfluorodecylphosphonic acid (Non-Patent Document 1), has been known.

PRIOR ART DOCUMENT

Non-Patent Document

Non-Patent Document 1: J. Phys. Chem. C, 2007, 111, 3956-3962

SUMMARY OF INVENTION

Technical Problem

However, according to findings by the present inventor, the surface layer described in Non-Patent Document 1 is insufficient in water/oil repellency, fingerprint stain removability and lubricity. Further, in a case where a substrate having the surface layer as described in Non-Patent Document 1 is repeatedly abraded, the water/oil repellency is substantially deteriorated due to the abrasion, whereby the abrasion resistance becomes insufficient.

The object of the present invention is to provide a surface treatment agent capable of imparting excellent water/oil repellency, fingerprint stain removability, abrasion resistance and lubricity to the substrate surface.

Solution to Problem

The present invention provides a surface treatment agent for a substrate, a coating agent, a substrate having a surface layer and a novel perfluoropolyether group-containing phosphate compound, which have the following constructions [1] to [14].

[1] A surface treatment agent for a substrate, comprising a perfluoropolyether group-containing phosphate compound.

[2] The surface treatment agent according to [1], wherein the perfluoropolyether group-containing phosphate compound is a compound represented by the following formula (1):

$$B^1—(C_mF_{2m}O)_{n1}-A^1 \quad (1)$$

wherein $A^1$ is a monovalent organic group having at least one phosphoric acid group at its terminal, $B^1$ is $R^{F1}$—O—, $D^1$-$Q^1$-O—$CH_2$— or $A^2$-O—, wherein $R^{F1}$ is a $C_{1-6}$ perfluoroalkyl group, $D^1$ is $CF_3$— or $CF_3$—O—, $Q^1$ is a $C_{1-20}$ fluoroalkylene group containing at least one hydrogen atom, a $C_{2-20}$ fluoroalkylene group containing at least one hydrogen atom and having an etheric oxygen atom between carbon-carbon atoms, a $C_{1-20}$ alkylene group, or a $C_{2-20}$ alkylene group having an etheric oxygen atom between carbon-carbon atoms, and $A^2$ is a monovalent organic group having at least one phosphoric acid group at its terminal, m is an integer of from 1 to 6, and n1 is an integer of from 1 to 200, provided that when n1 is at least 2, $(C_mF_{2m}O)_{n1}$ may be one composed of at least two types of $(C_mF_{2m}O)$ different in m.

[3] The surface treatment agent according to [2], wherein said $(C_mF_{2m}O)_{n1}$ is a group represented by the following formula (2-1):

$$(C_rF_{2r}O)_{n2}(C_sF_{2s}O)_{n3} \quad (2\text{-}1)$$

wherein r is an integer of from 1 to 3, s is an integer of from 3 to 6, provided that r and s are not 3 at the same time, n2 is an integer of at least 1, n3 is an integer of at least 1, provided that n2+n3 is an integer of from 2 to 200, and a bonding order of $(C_rF_{2r}O)$ and $(C_sF_{2s}O)$ is not limited.

[4] The surface treatment agent according to [2], wherein said $(C_mF_{2m}O)_{n1}$ is a group represented by the following formula (2-2):

$$(CF_2O)_{n7}(CF_2CF_2O)_{n8} \quad (2\text{-}2)$$

wherein n7 is an integer of at least 1, n8 is an integer of at least 1, provided that n7+n8 is an integer of from 2 to 200, and a bonding order of $(CF_2O)$ and $(CF_2CF_2O)$ is not limited.

[5] The surface treatment agent according to any one of [2] to [4], wherein said $A^1$ is a group represented by the following formula (3):

$$\text{-}Q^{F1}(CX_2)_{w1}\text{-}E^1\text{-}Y^1\text{—}O\text{—}P(=O)(OH)_2 \quad (3)$$
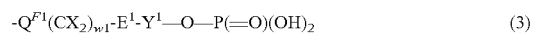

wherein $Q^{F1}$ is a $C_{1-20}$ perfluoroalkylene group, $CX_2$ is $CH_2$ or CHF, w1 is 0 or 1, $E^1$ is a single bond, —C(=O)NH— (provided that $Y^1$ is bonded to N), —OC(=O)NH— (provided that $Y^1$ is bonded to N), —O—, —C(=O)O— (provided that $Y^1$ is bonded to O), —OC(=O)O—, —NHC(=O)NH— or —NHC(=O)O— (provided that $Y^1$ is bonded to O), wherein $Y^1$ is an alkylene group, a poly(oxyalkylene)-alkylene group, a cycloalkylene group, an arylene group, or an alkylene group in which at least one of hydrogen atoms is substituted by a hydroxy group, provided that $E^1$ is not —O—, —OC(=O)NH— or —OC(=O)O— when w1 is 0, and $Y^1$ is not an alkylene group when w1 is 1, $CX_2$ is $CH_2$ and $E^1$ is a single bond.

[6] The surface treatment agent according to any one of [2] to [5], wherein said $Q^1$ is a group represented by the following formula (4-1), (4-2) or (4-3):

$$\text{-}Q^{F2}\text{-}O\text{—}CHFCF_2\text{—} \quad (4\text{-}1)$$

$-Q^{F2}-CHFCF_2-$ (4-2)

$-Q^{F2}-C_zH_{2z}-$ (4-3)

wherein $Q^{F2}$ is a single bond, a $C_{1-15}$ perfluoroalkylene group, or a $C_{2-15}$ perfluoroalkylene group having an etheric oxygen atom between carbon-carbon atoms, $Q^{F2}$ is bonded to said $D^1$, and z is an integer of from 1 to 4, provided that $Q^{F2}$ is not a single bond in the formula (4-1) and (4-2) when said $D^1$ s $CF_3-O-$.

[7] The surface treatment agent according to any one of [2] to [6], wherein the number average molecular weight (Mn) of the compound represented by the formula (1) is 2,000 to 10,000.

[8] The surface treatment agent according to any one of [2] to [7], which contains the compound represented by the formula (1) wherein said $B^1$ is $R^{F1}-O-$ or $D^1-Q^1-O-CH_2-$.

[9] The surface treatment agent according to any one of [2] to [7], which contains the compound represented by the formula (1) wherein said $B^1$ is $R^{F1}-O-$ or $D^1-Q^1-O-CH_2-$ and the compound represented by the formula (1) wherein said $B^1$ is $A^2-O-$.

[10] The surface treatment agent according to [9], wherein the content of the compound represented by the formula (1) wherein said $B^1$ is $A^2-O-$, is from 10 to 60 parts by mass, per 100 parts by mass in total of the compound represented by the formula (1) wherein said $B^1$ is $R^{F1}-O-$ or $D^1-Q^1-O-CH_2-$.

[11] The surface treatment agent according to any one of [1] to [10], wherein said substrate is a sapphire substrate.

[12] A coating agent comprising the surface treatment agent as defined in any one of [1] to [11] and a liquid medium.

[13] A substrate having a surface layer formed from the surface treatment agent as defined in any one of [1] to [11] or the coating agent as defined in [12].

[14] A compound represented by the following formula (1):

$B^1-(C_mF_{2m}O)_{n1}-A^1$ (1)

wherein $A^1$ is a monovalent organic group having at least one phosphoric acid group at its terminal, $B^1$ is $R^{F1}-O-$, $D^1-Q^1-O-CH_2-$ or $A^2-O-$, wherein $R^{F1}$ is a $C_{1-6}$ perfluoroalkyl group, $D^1$ is $CF_3-$ or $CF_3-O-$, $Q^1$ is a $C_{1-20}$ fluoroalkylene group containing at least one hydrogen atom, a $C_{2-20}$ fluoroalkylene group containing at least one hydrogen atom and having an etheric oxygen atom between carbon-carbon atoms, a $C_{1-20}$ alkylene group, or a $C_{2-20}$ alkylene group having an etheric oxygen atom between carbon-carbon atoms, $A^2$ is a monovalent organic group having at least one phosphoric acid group at its terminal, m is an integer of from 1 to 6, and n1 is an integer of from 1 to 200, provided that when n1 is at least 2, $(C_mF_{2m}O)_{n1}$ may be one composed of at least two types of $(C_mF_{2m}O)$ different in m.

Advantageous Effects of Invention

According to the surface treatment agent of the present invention, it is possible to impart excellent water/oil repellency, fingerprint stain removability, abrasion resistance and lubricity, to the substrate surface.

DETAILED DESCRIPTION OF INVENTION

[Definition of Terms]

In this specification, a compound represented by the formula (1) will be also referred to as compound (1). The same applies to compounds represented by other formulae.

The following definitions of terms will be applied to the entire specification including the claims.

An "etheric oxygen atom" means an oxygen atom to form an ether bond (—O—) between carbon-carbon atoms.

A "perfluoroalkyl group" means a group having all of hydrogen atoms in an alkyl group substituted by fluorine atoms.

A "fluoroalkylene group" means a group having some or all of hydrogen atoms in an alkylene group substituted by fluorine atoms, and a "perfluoroalkylene group" means a group having all of hydrogen atoms in an alkylene group substituted by fluorine atoms. Here, a "fluoroalkylene group" includes a "perfluoroalkylene group".

A "perfluoropolyether" means a group formed of at least two oxyperfluoroalkylene units. Here, the chemical formula of oxyperfluoroalkylene represents one having its oxygen atom arranged on the right side of a perfluoroalkylene group.

A "phosphoric acid group" means $-O-P(=O)(OH)_2$.

An "organic group" means a group having at least one carbon atom.

A "perfluoropolyether group-containing phosphate compound" means a compound having a perfluoropolyether group and a phosphoric acid group.

A "surface layer" means a layer to be formed on the substrate surface by treating the substrate surface with the surface treatment agent of the present invention. The "surface layer" is present for imparting excellent water/oil repellency, fingerprint stain removability, abrasion resistance and lubricity to the substrate surface.

[Perfluoropolyether Group-Containing Phosphate Compound]

The surface treatment agent of the present invention (hereinafter also referred to as "the present surface treatment agent") contains a perfluoropolyether group-containing phosphate compound (hereinafter also referred to as "the present compound"). The present surface treatment agent may contain one type of the present compound or at least two types of the present compound.

The present compound, which has a perfluoropolyether group, can impart excellent water/oil repellency, fingerprint stain removability and lubricity to the substrate surface, when used as the present surface treatment agent containing the present compound. Further, when used as the present surface treatment agent containing the present compound, it can impart excellent abrasion resistance to the substrate surface, whereby it is possible to suppress deterioration of water/oil repellency due to abrasion even if the substrate surface is repeatedly rubbed. Here, at least two oxyperfluoroalkylene units composing the perfluoropolyether group may be the same or different. Further, each oxyperfluoroalkylene unit may be linear or branched, but is preferably linear since it is possible to impart more excellent oil repellency to the substrate surface.

The present compound is a compound in which an organic group having at least one phosphoric acid group bonded to only one terminal of the perfluoropolyether group, or a compound having organic groups each having at least one phosphoric acid group bonded to both terminals of the perfluoropolyether group. The present surface treatment agent preferably contains, as an essential component, the present compound having an organic group having at least one phosphoric acid group bonded to only one terminal of the perfluoropolyether group, since one terminal of the perfluoropolyether group becomes a free terminal which imparts excellent fingerprint stain removability to the substrate surface. Accordingly, the present surface treatment agent is particularly preferably one containing the present compound having an organic group having at least one phosphoric acid group bonded to only one terminal of the perfluoropolyether group, or one containing a mixture of the present compound having an organic group having at least one phosphoric acid group bonded to only one terminal of the perfluoropolyether group with the present compound having organic groups each having at least one phosphoric acid group bonded to both terminals of the perfluoropolyether group.

(Compound (1))

Specifically, the present compound is preferably a compound represented by the formula (1):

wherein $A^1$ is a monovalent organic group having at least one phosphoric acid group at its terminal, $B^1$ is $R^{F1}$—O—, $D^1$-$Q^1$-O—$CH_2$— or $A^2$-O—, wherein $R^{F1}$ is a $C_{1-6}$ perfluoroalkyl group, $D^1$ is $CF_3$— or $CF_3$—O—, $Q^1$ is a $C_{1-20}$ fluoroalkylene group containing at least one hydrogen atom, a $C_{2-20}$ fluoroalkylene group containing at least one hydrogen atom and having an etheric oxygen atom between carbon-carbon atoms, a $C_{1-20}$ alkylene group, or a $C_{2-20}$ alkylene group having an etheric oxygen atom between carbon-carbon atoms, and $A^2$ is a monovalent organic group having at least one phosphoric acid group at its terminal, m is an integer of from 1 to 6, and n1 is an integer of from 1 to 200, provided that when n1 is at least 2, $(C_mF_{2m}O)_{n1}$ may be one composed of at least two types of $(C_mF_{2m}O)$ different in m.

<$(C_mF_{2m}O)_{n1}$>

$(C_mF_{2m}O)_{n1}$ is a perfluoropolyether group. Therefore, by using compound (1), is possible to impart excellent water/oil repellency, fingerprint stain removability and lubricity to the substrate surface.

m is an integer of from 1 to 6. $(C_mF_{2m}O)$ may be linear or branched. $(C_mF_{2m}O)$ may, for example, be $(CF_2O)$, $(CF_2CF_2O)$, $(CF(CF_3)O)$, $(CF_2CF_2CF_2O)$, $(CF(CF_3)CF_2O)$, $(CF_2CF(CF_3)O)$, $(CF_2CF_2CF_2CF_2O)$, $(CF(CF_3)CF_2CF_2O)$, $(CF_2CF(CF_3)CF_2O)$ or $(CF_2CF_2CF(CF_3)O)$.

With a view to imparting excellent water/oil repellency, fingerprint stain removability and lubricity to the substrate surface, n1 is a integer of at least 2, preferably an integer of at least 4, particularly preferably an integer of at least 5. With a view to imparting more excellent abrasion resistance to the substrate surface, and further with a view to exhibiting excellent compatibility when other components are blended into the present surface treatment agent, n1 is preferably an integer of at most 100, more preferably an integer of at most 80, particularly preferably an integer of at most 60. When the present surface treatment agent contains at least two types of compound (1), n1 is an average value. In such a case, n1 may not be an integer. When n1 is at least 2, $(C_mF_{2m}O)_{n1}$ may be one composed of at least two types of $C_mF_{2m}O$ different in m. In such a case, a bonding order of $C_mF_{2m}O$ is not restricted. For example, in a case where $CF_2O$ (m is 1) and $CF_2CF_2O$ (m is 2) are present, $CF_2O$ and $CF_2CF_2O$ may be randomly arranged, $CF_2O$ and $CF_2CF_2O$ may be alternately arranged, or a block composed of a plurality of $CF_2O$ and a block composed of a plurality of $CF_2CF_2O$ may be linked.

<<Preferable First $(C_mF_{2m}O)_{n1}$>>

$(C_mF_{2m}O)_{n1}$ is preferably a group represented by the following formula (2-1) with a view to imparting more excellent water/oil repellency and abrasion resistance to the substrate surface.

wherein r is an integer of from 1 to 3, s is an integer of from 3 to 6, provided that r and s are not 3 at the same time, n2 is an integer of at least 1, n3 is an integer of at least 1, provided that n2+n3 is an integer of from 2 to 200, and a bonding order of $(C_rF_{2r}O)$ and $(C_sF_{2s}O)$ is not limited.

With a view to imparting more excellent fingerprint stain removability to the substrate surface, n2 is preferably an integer of at least 3, particularly preferably an integer of at least 5. With a view to exhibiting excellent compatibility when other components are blended into the present surface treatment agent, n2 is preferably an integer of at most 20, particularly preferably an integer of at most 10.

With a view to imparting more excellent water/oil repellency to the substrate surface, n3 is preferably an integer of at least 3, particularly preferably an integer of at least 5. With a view to exhibiting excellent compatibility when other components are blended into the present surface treatment agent, n3 is preferably an integer of at most 20, particularly preferably an integer of at most 10.

With a view to imparting more excellent abrasion resistance to the substrate surface while the number of phosphoric acid groups present per unit molecular weight of compound (1) would not be too small, and further with a view to exhibiting excellent compatibility when other components are blended into the present surface treatment agent, n2+n3 is preferably an integer of from 2 to 100, more preferably an integer of from 2 to 40, particularly preferably an integer of from 2 to 20.

Further, with a view to imparting more excellent water/oil repellency and abrasion resistance to the substrate surface, preferred is a group of the formula (2-1) wherein r is 2 and s is 4, more preferred is a group represented by the following formula (2-1-a), particularly preferred is a group represented by the following formula (2-1-b):

wherein n4 is an integer of at least 1, n5 is an integer of at least 1, provided that n4+n5 is an integer of from 2 to 200, and $(C_2F_4O)$ and $(C_4F_8O)$ are alternately arranged.

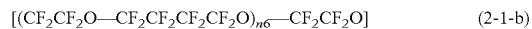

wherein n6 is an integer of from 1 to 99.

n6 is preferably an integer of from 1 to 20, particularly preferably an integer of from 1 to 10.

<<Preferable Second $(C_mF_{2m}O)_{n1}$>>

With a view to imparting more excellent lubricity to the substrate surface, $(C_mF_{2m}O)_{n1}$ is preferably a group represented by the following formula (2-2):

wherein n7 is an integer of at least 1, n8 is an integer of at least 1, provided that n7+n8 is an integer of from 2 to 200, and a bonding order of $(CF_2O)$ and $(CF_2CF_2O)$ is not limited.

$(CF_2O)_{n7}(CF_2CF_2O)_{n8}$, which is an oxyperfluoroalkylene group having a small number of carbon atoms, is excellent in flexibility. Therefore, it is possible to impart more excellent lubricity to the substrate surface. Especially, $(CF_2O)_{n7}$, which is a group having an oxygen atom and a number of carbon atoms being 1, is more excellent in flexibility.

With a view to imparting more excellent water/oil repellency, fingerprint stain removability and lubricity to the substrate surface, n7 is preferably an integer of at least 2, particularly preferably an integer of at least 3. With a view to imparting more excellent abrasion resistance to the substrate surface while the number of phosphoric acid groups present per unit molecular weight of compound (1) would not be too small, and further with a view to exhibiting excellent compatibility when other components are blended into the present surface treatment agent, n7 is preferably an integer of at most 50, more preferably an integer of at most 40, particularly preferably an integer of at most 30.

With a view to imparting more excellent water/oil repellency, fingerprint stain removability and lubricity to the substrate surface, n8 is preferably an integer of at least 2. With a view to imparting more excellent abrasion resistance to the substrate surface while the number of phosphoric acid groups present per unit molecular weight of compound (1) would not be too small, and further with a view to exhibiting excellent compatibility when other components are blended into the present surface treatment agent, n8 is preferably an integer of at most 50, more preferably an integer of at most 40, particularly preferably an integer of at most 30.

n7+n8 is preferably an integer of from 2 to 100, more preferably an integer of from 2 to 80, particularly preferably an integer of from 2 to 60.

Further, with a view to imparting more excellent lubricity to the substrate surface, the ratio of n7 to n8 is preferably more than 0 time and at most three times, particularly preferably from 1 to 2 times.

<$A^1$>

$A^1$ is a monovalent organic group having at least one phosphoric acid group at its terminal. Since $A^1$ has a phosphoric acid group, by using compound (1), it is possible to impart excellent water/oil repellency, fingerprint stain removability and abrasion resistance to the substrate surface.

The number of phosphoric acid groups in $A^1$ is from 1 to 3, preferably 1 or 2, particularly preferably 1.

When the number of phosphoric acid groups is 1, $A^1$ is preferably a group represented by the following formula (3):

$$-Q^{F1}(CX_2)_{w1}-E^1-Y^1-O-P(=O)(OH)_2 \quad (3)$$

wherein $Q^{F1}$ is a $C_{1-20}$ perfluoroalkylene group, $CX_2$ is $CH_2$ or CHF, w1 is 0 or 1, $E^1$ is a single bond, —C(=O)NH— (provided that $Y^1$ is bonded to N), —OC(=O)NH— (provided that $Y^1$ is bonded to N), —O—, —C(=O)O— (provided that $Y^1$ is bonded to O), —OC(=O)O—, —NHC(=O)NH— or —NHC(=O)O— (provided that $Y^1$ is bonded to 0), wherein $Y^1$ is an alkylene group, a poly(oxyalkylene)-alkylene group, a cycloalkylene group, an arylene group, or an alkylene group in which at least one of hydrogen atoms is substituted by a hydroxy group, provided that $E^1$ is not —O—, —OC(=O)NH— or —OC(=O)O— when w1 is 0, and $Y^1$ is not an alkylene group when w1 is 1, $CX_2$ is $CH_2$ and $E^1$ is a single bond.

$QF^1$ is a $C_{1-20}$ perfluoroalkylene group. The perfluoroalkylene group may be linear or branched. With a view to imparting excellent fingerprint stain removability to the substrate surface, $Q^{F1}$ is preferably a $C_{1-6}$ perfluoroalkylene group, more preferably a $C_{1-3}$ perfluorolalkylene group, particularly preferably the following perfluoroalkylene group.

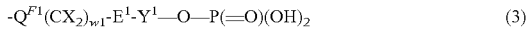

$Y^1$ is an alkylene group, a poly(oxyalkylene)-alkylene group, a cycloalkylene group, an arylene group or an alkylene group in which at least one of hydrogen atoms is substituted by a hydroxy group. The number of carbon atoms of "alkylene" in the alkylene group and the poly(oxyalkylene)-alkylene group, is preferably from 2 to 6, particularly preferably from 2 to 4. From the viewpoint of easiness of production of compound (1), $Y^1$ is preferably an alkylene group or a poly(oxyalkylene)-alkylene group.

$Y^1$ is particularly preferably the following groups, wherein p1 and q1 are an integer of from 1 to 20, preferably an integer of from 1 to 10, particularly preferably an integer of from 1 to 3.

—$CH_2CH_2$—,
—$CH_2CH(CH_3)$—,
—$CH_2CH_2CH_2$—,
—$CH_2CH_2CH_2CH_2$—,
—$(CH_2CH_2O)_{p1}$—$CH_2CH_2$— or
—$(CH_2CH(CH_3)O)_{q1}$—$CH_2CH(CH_3)$—.

<<Preferred $A^1$>>

From the viewpoint of easiness of production of compound (1), $A^1$ is particularly preferably a group represented by the following formula (3-1) or (3-2). Here, the above preferred examples will be applied to $Q^{F1}$ and $Y^1$.

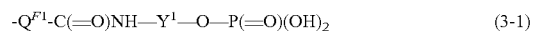

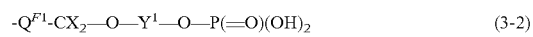

<$B^1$>

$B^1$ is $R^{F1}$—O—, $D^1$-$Q^1$-O—$CH_2$— or $A^2$-O—.

The present compound having an organic group having at least one phosphoric acid group bonded to only one terminal of the perfluoropolyether group, is compound (1) wherein $B^1$ is $R^{F1}$—O— or $D^1$-$Q^1$-O—$CH_2$—, and the present compound having organic groups each having at least one phosphoric acid group respectively bonded to both terminals of the perfluoropolyether group, is compound (1) wherein $B^1$ is $A^2$-O—.

$B^1$ is preferably $R^{F1}$—O— or $D^1$-$Q^1$-O—$CH_2$—. When $B^1$ is $R^{F1}$—O— or $D^1$-$Q^1$-O—$CH_2$—, one terminal of compound (1) is $CF_3$—. Therefore, by using compound (1) having $R^{F1}$—O— or $D^1$-$Q^1$-O—$CH_2$— on the substrate surface, it is possible to impart excellent fingerprint stain removability to the substrate surface.

On the other hand, when $B^1$ is $A^2$-O—, the number of phosphoric acid groups capable of reacting with a substrate will increase at both terminals of compound (1), whereby it is possible to impart more excellent abrasion resistance to the substrate surface.

<<$R^{F1}$>>

$R^{F1}$ is a $C_{1-6}$ perfluoroalkyl group. The perfluoroalkyl group may be linear or branched. As a specific example of $R^{F1}$, $CF_3$—, $CF_3CF_2$—, $CF_3(CF_2)_2$—, $CF_3(CF_2)_3$—, $CF_3(CF_2)_4$—, $CF_3(CF_2)_5$— or $CF_3CF(CF_3)$— may be mentioned. With a view to imparting more excellent water/oil repellency and fingerprint stain removability to the substrate surface, $R^{F1}$ is preferably a $C_{1-4}$ linear perfluoroalkyl group ($CF_3$—, $CF_3CF_2$—, $CF_3(CF_2)_2$— or $CF_3(CF_2)_3$—).

<<$Q^1$>>

$Q^1$ is a $C_{1-20}$ fluoroalkylene group containing at least one hydrogen atom, a $C_{2-20}$ fluoroalkylene group containing at least one hydrogen atom and having an etheric oxygen atom between carbon-carbon atoms, a $C_{1-20}$ alkylene group, or a $C_{2-20}$ alkylene group having an etheric oxygen atom between carbon-carbon atoms. The number of hydrogen atoms in $Q^1$ is at least 1, preferably at least 2, particularly preferably at least 3.

$Q^1$ is preferably a single bond, or a group represented by the following formula (4-1), (4-2) or (4-3) in view of easiness of production of compound (1) wherein $B^1$ is $D^1$-$Q^1$-O—$CH_2$—.

wherein -$Q^{F2}$ is a single bond, a $C_{1-15}$ perfluoroalkylene group, or a $C_{2-15}$ perfluoroalkylene group having an etheric oxygen atom between carbon-carbon atoms, $Q^{F2}$ is bonded to said $D^1$, and z is an integer of from 1 to 4, provided that $Q^{F2}$ is not a single bond in the formula (4-1) and (4-2) when said $D^1$ is $CF_3$—O—.

With a view to sufficiently imparting fingerprint stain removability or lubricity to the substrate surface, $Q^{F2}$ is preferably a $C_{1-9}$ perfluoroalkylene group or a $C_{2-13}$ perfluoroalkylene group having an etheric oxygen atom between carbon-carbon atoms. Here, the perfluoroalkylene group may be linear or branched. z is preferably an integer of from 1 to 3, and when z is at least 3, $C_zH_{2z}$ may be linear or branched, but is preferably linear.

In a case where $Q^1$ is a group represented by the formula (4-1), a specific example of the $D^1$-$Q^1$- group includes the following.

$CF_3$—O—$CHFCF_2$—,
$CF_3$—$CF_2$—O—$CHFCF_2$—,
$CF_3$—$CF_2CF_2$—O—$CHFCF_2$—,
$CF_3$—$CF_2CF_2CF_2$—O—$CHFCF_2$—,
$CF_3$—$CF_2CF_2CF_2CF_2CF_2$—O—$CHFCF_2$—,
$CF_3$-Q-$CF_2CF_2$—O—$CHFCF_2$—,
$CF_3$—$CF_2OCF_2CF_2$—O—O—$CHFCF_2$—,
$CF_3$—O—$CF_2CF_2OCF_2CF_2$—O—$CHFCF_2$—,
$CF_3$—$CF_2OCF_2CF_2OCF_2CF_2$—O—$CHFCF_2$—,
$CF_3$—$CF_2CF_2OCF(CF_3)CF_2$—O—$CHFCF_2$—,
$CF_3$—$CF_2CF_2OCF(CF_3)CF_2OCF(CF_3)CF_2$—O—$CHFCF_2$—.

In a case where $Q^1$ is a group represented by the formula (4-2), a specific example of the $D^1$-$Q^1$- group includes the following.

$CF_3$—$CHFCF_2$—,
$CF_3$—$CF_2$—$CHFCF_2$—,
$CF_3$—$CF_2CF_2$—$CHFCF_2$—,
$CF_3$—$CF_2CF_2CF_2$—$CHFCF_2$—.

In a case where $Q^1$ is a group represented by the formula (4-3), a specific example of the $D^1$-$Q^1$- group includes the following.

$CF_3$—$CH_2$—,
$CF_3$—$CF_2$—$CH_2$—,
$CF_3$—$CF_2CF_2$—$CH_2$—,
$CF_3$—$CF_2CF_2CF_2$—$CH_2$—,
$CF_3$—$CF_2CF_2CF_2CF_2$—$CH_2$—,
$CF_3$—$CF_2CF_2CF_2CF_2CF_2$—$CH_2$—,
$CF_3$—$CF_2CF_2CF_2CF_2CF_2CF_2$—$CH_2$—,
$CF_3$—$CH_2CH_2$—,
$CF_3$—$CF_2$—$CH_2CH_2$—,
$CF_3$—$CF_2CF_2$—$CH_2CH_2$—,
$CF_3$—$CF_2CF_2CF_2$—$CH_2CH_2$—,
$CF_3$—$CF_2CF_2CF_2CF_2$—$CH_2CH_2$—,
$CF_3$—$CF_2CF_2CF_2CF_2CF_2$—$CH_2CH_2$—,
$CF_3$—$CF_2CF_2CF_2CF_2CF_2CF_2$—$CH_2CH_2$—,
$CF_3$—$CH_2CH_2CH_2$—,
$CF_3$—$CF_2$—$CH_2CH_2CH_2$—,
$CF_3$—$CF_2CF_2$—$C_2CH_2CH_2$—,
$CF_3$—$CF_2CF_2CF_2$—$CH_2CH_2CH_2$—,
$CF_3$—$CF_2CF_2CF_2CF_2$—$CH_2CH_2CH_2$—,
$CF_3$—$CF_2CF_2CF_2CF_2CF_2$—$CH_2CH_2CH_2$—,
$CF_3$—$CF_2CF_2CF_2CF_2CF_2CF_2$—$CH_2CH_2CH_2$—,
$CF_3$—O—$CF_2$—$CH_2$—,
$CF_3$—$CF_2OCF_2$—$CH_2$—,
$CF_3$—O—$CF_2CF_2OCF_2$—$CH_2$—,
$CF_3$—$CF_2OCF_2CF_2OCF_2$—$CH_2$—,
$CF_3$—O—$CF_2CF_2OCF_2CF_2OCF_2$—$CH_2$—,
$CF_3$—$CF_2OCF_2CF_2OCF_2CF_2OCF_2$—$CH_2$—.

$Q^1$ is preferably a group represented by the formula (4-1) in view of easiness of production of compound (1) wherein $B^1$ is $D^1$-$Q^1$-O—$CH_2$—, and the $D^1$-$Q^1$- group is preferably $CF_3$—$CF_2CF_2$—O—$CHFCF_2$— or $CF_3$—$CF_2CF_2CF_2CF_2$—O—$CHFCF_2$—, particularly preferably $CF_3$—$CF_2CF_2$—O—$CHFCF_2$—.

<<$A^2$>>

$A^2$ is a monovalent organic group having at least one phosphoric acid group at its terminal. The above description relating to $A^1$ including preferred examples, will be also applied to examples of $A^2$.

<Preferred Embodiments of Compound (1)>

Compound (1) wherein $B^1$ is $R^{F1}$—O— is preferably the following compound (1a-1). Further, compound (1) wherein $B^1$ is $D^1$-$Q^1$-O—$CH_2$— is preferably the following compound (1a-2).

<Compound (1a-1)>

$$R^{F2}\text{—O—}[(C_2F_4O)_{n9}(C_4F_8O)_{n10}]\text{-}A^3 \qquad (1a\text{-}1)$$

wherein n9 is an integer of at least 1, n10 is an integer of at least 1, provided that n9+n10 is an integer of from 2 to 200, $(C_2F_4O)$ and $(C_4F_8O)$ are alternately arranged, $R^{F2}$ is a $C_{1-6}$ perfluoroalkyl group, and $A^3$ is a monovalent organic group having at least one phosphoric acid group at its terminal.

By using compound (1a-1), the present surface treatment agent can impart more excellent water/oil repellency to the substrate surface.

With a view to imparting more excellent water/oil repellency to the substrate surface, $(C_2F_4O)$ and $(C_4F_8O)$ are preferably $(CF_2CF_2O)$ and $(CF_2CF_2CF_2CF_2O)$.

The above description relating to n2 including preferred examples, will be also applied to n9.

The above description relating to n3 including preferred examples, will be also applied to n10.

With a view to imparting more excellent water/oil repellency and abrasion resistance to the substrate surface, $[(C_2F_4O)_{n9}(C_4F_8O)_{n10}]$ is preferably a group represented by the above formula (2-1-b).

The above description relating to $R^{F1}$ including preferred examples, will be also applied to examples of $R^{F2}$. With a view to imparting more excellent fingerprint stain removability to the substrate surface, $R^{F2}$ is particularly preferably $CF_3$— or $CF_3CF_2$—.

The above description relating to $A^1$ including preferred examples, will be also applied to examples of $A^3$. $A^3$ is particularly preferably a group represented by the formula (3-1).

With a view to imparting particularly excellent water/oil repellency and abrasion resistance to the substrate surface, compound (1a-1) is preferably a compound (1a-1-1).

$$CF_3\text{—O—}[(CF_2CF_2O\text{—}CF_2CF_2CF_2CF_2O)_{n11}\text{—}\\CF_2CF_2O]\text{—}CF_2CF_2CF_2\text{—C(=O)NH—}\\CH_2CH_2\text{—O—P(=O)(OH)}_2 \qquad (1a\text{-}1\text{-}1)$$

wherein n11 is an integer of from 1 to 99.

The above description relating to n6 including preferred examples, will be also applied to n11.

<Compound (1a-2)>

$$D^2\text{-}Q^2\text{-O—}CH_2\text{—}(C_vF_{2v}O)_{n12}\text{-}A^4 \qquad (1a\text{-}2)$$

wherein $D^2$ is $CF_3$— or $CF_3$—O—, and $Q^2$ is a $C_{1-20}$ fluoroalkylene group containing at least one hydrogen atom, a $C_{2-20}$ fluoroalkylene group containing at least one hydrogen atom and having an etheric oxygen atom between carbon-carbon atoms, a $C_{1-20}$ alkylene group, or a $C_{2-20}$ alkylene group having an etheric oxygen atom between carbon-carbon atoms, v is an integer of from 1 to 6, n12 is an integer of from 1 to 200, provided that when n12 is at least 2, $(C_vF_{2v}O)_{n12}$ may be one composed of at least two types of $(C_vF_{2v}O)$ different in v, and $A^4$ is a monovalent organic group having at least one phosphoric acid group at its terminal.

Compound (1a-2), which contains a $CH_2$ group (the $CH_2$ group is more improved in flexibility than a $CF_2$ group) having hydrogen atoms with a small atomic radius in its molecule, is more improved in flexibility. Therefore, the present surface treatment agent, which uses compound (1a-2), can impart more excellent abrasion resistance and lubricity to the substrate surface.

The above description relating to $(C_mF_{2m}O)_{n1}$ including preferred examples, will be also applied to examples of $(C_vF_{2v}O)_{n12}$, and $(CvF_{2v}O)_{n12}$ is particularly preferably a preferable second $(C_mF_{2m}O)_{n1}$.

The above description relating to $Q^1$ including preferred examples, will be also applied to examples of $Q^2$, provided that when $Q^2$ is a group represented by the formula (4-1), (4-2) or (4-3), $Q^{F2}$ in the formula (4-1), (4-2) or (4-3) is bonded to $D^2$, and further when $D^2$ is $CF_3$—O—, $Q^{F2}$ in the formula (4-1) or (4-2) is not a single bond.

The above description relating to $A^1$ including preferred examples, will be also applied to examples of $A^4$. $A^4$ is particularly preferably a group represented by the formula (3-2).

With a view to imparting particularly excellent abrasion resistance and lubricity to the substrate surface, compound (1a-2) is preferably compound (1a-2-1).

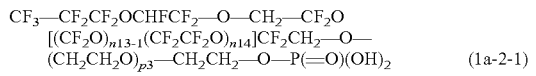

wherein n13 is an integer of at least 1, n14 is an integer of at least 1, provided that n13+n14 is an integer of from 2 to 200, the bonding order of $(CF_2O)$ and $(CF_2CF_2O)$ is not limited, and p3 is an integer of 0 or 1 to 20.

The above description relating to p2 including preferred examples, will be also applied to p3.

The number average molecular weight (Mn) of the present compound is preferably from 2,000 to 10,000, more preferably from 2,500 to 8,000, particularly preferably from 3,000 to 6,000. When it is within the above range, excellent water/oil repellency, fingerprint stain removability and lubricity can be imparted to the substrate surface, and further, compatibility with other components can be excellent when such other components are blended into the present surface treatment agent.

The number average molecular weight of the present compound is calculated by the following method by means of NMR analysis.

The number average molecular weight is calculated by determining the number (average value) of oxyperfluoroalkylene groups based on the terminal group, by means of $^1$H-NMR or $^{19}$F-NMR. The terminal group is, for example, $B^1$ or $A^1$ in the formula (1).

[Process for Producing Compound (1)]

A process for producing compound (1) will be explained, with reference to the compounds represented by the formula (1a-1-2) and the formula (1a-2-2).

(Process for Producing Compound (1a-1-2))

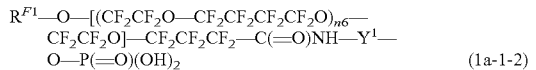

Compound (12a) is subjected to hydrogen reduction by using a reducing agent (such as sodium borohydride or lithium aluminum hydride) to obtain compound (11a).

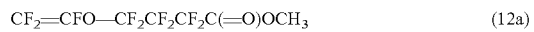

Compound (11a) and an alcohol (such as methanol, ethanol, 1-propanol, 2-propanol, 2,2,2-trifluoroethanol, 2,2,3,3-tetrafluoropropanol or 1,1,1,3,3,3-hexafluoro-2-propanol, hereinafter referred to as $R^{f1}$—OH, wherein $R^{f1}$ is a $C_{1-6}$ fluoroalkyl group or a $C_{1-6}$ alkyl group) are reacted in the presence of a base or a quaternary ammonium salt (such as potassium carbonate, sodium carbonate, sodium fluoride, potassium fluoride, cesium fluoride, sodium hydride, potassium tert-butoxide, sodium hydroxide, potassium hydroxide, tetrabutylammonium chloride or tetrabutylammonium bromide) to obtain compound (10a).

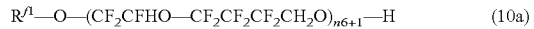

By controlling the amount of $Rf^1$—OH to be added to compound (11a), it is possible to synthesize compound (10a) having a desired number average molecular weight. Further, $Rf^1$—OH may be compound (11a) itself, and by controlling the reaction time or by separation-purification of the product, it is possible to synthesize compound (10a) having a desired number average molecular weight.

The synthesis of compound (11a) and the synthesis of compound (10a) by the polyaddition reaction can be carried out by a known method disclosed in U.S. Pat. No. 5,134,211.

Compound (10a) and $ClC(=O)R^1$ are subjected to an esterification reaction to obtain compound (9a). Here, $R^1$ is a $C_{1-11}$ alkyl group, a $C_{1-11}$ fluoroalkyl group, a $C_{2-11}$ alkyl group having an etheric oxygen atom between carbon-carbon atoms or a $C_{2-11}$ fluoroalkyl group having an etheric oxygen atom between carbon-carbon atoms. The fluoroalkyl group is preferably a perfluoroalkyl group.

Further, by means of fluorine gas, hydrogen atoms in compound (9a) are substituted by fluorine atoms to obtain compound (7a). Here, when $R^1$ is a group having a hydrogen atom, $R^{F4}$ is a group having all of the hydrogen atoms contained in $R^1$ substituted by fluorine atoms, and when $R^1$ is a group having no hydrogen atoms, $R^{F4}$ is the same group as $R^1$, which is a perfluoroalkyl group or a $C_{2-11}$ perfluoroalkyl group having an etheric oxygen atom between carbon-carbon atoms. $R^{F1}$ is a group having all of the hydrogen atoms contained in $R^{f1}$ substituted by fluorine atoms. Such a fluorination step can be carried out, for example, in accordance with a method disclosed in WO2000/56694.

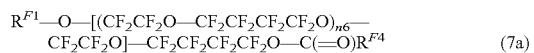

Compound (7a) and an alcohol (such as methanol, ethanol, 1-propanol or 2-propanol, hereinafter referred to as $R^2OH$, wherein $R^2$ is an alkyl group) are reacted to obtain compound (6a) represented by the following formula (6a).

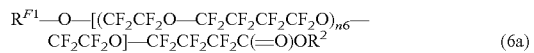

Compound (6a) and $H_2N$—$Y^1$—OH are reacted to obtain compound (5a).

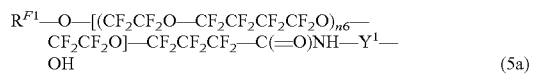

Compound (5a) and phosphorus oxychloride or diphosphorus pentoxide are reacted, followed by hydrolysis to obtain compound (1a-1-1).

Further, it is also possible to obtain compound (1a-1-1) by reacting compound (6a) with $NH_2—Y^1—OP(=O)(OH)_2$.

(Process for Producing Compound (1a-2-2))

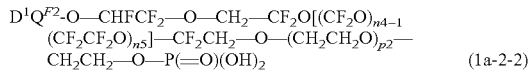
(1a-2-2)

wherein p2 is an integer of 0 or 1 to 20. p2 is preferably an integer of 0 or 1 to 10, particularly preferably an integer of 0 or 1 to 3.

In the presence of a basic compound, $D^1Q^{F2}$-O—CF=CF$_2$ is reacted with compound (4a-2) having OH groups at both terminals to obtain a mixture of compound (3a-2), compound (3a-2-2) and unreacted compound (4a-2).

(4a-2)

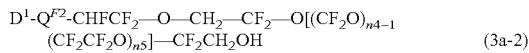
(3a-2)

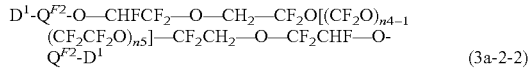
(3a-2-2)

From the above mixture, the monofunctional compound (3a-2) having a OH group remaining at its one terminal, is isolated, and in the presence of a basic compound such as cesium carbonate, ethylene carbonate is added to compound (3a-2) while conducting decarboxylation, to obtain compound (2a-2).

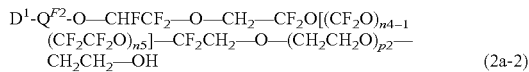
(2a-2)

Compound (2a-2) and phosphorus oxychloride or diphosphorus pentoxide are reacted, followed by hydrolysis to obtain compound (1a-2-2).

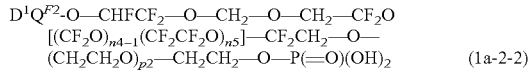
(1a-2-2)

[Surface Treatment Agent]

The present surface treatment agent contains the present compound. The present surface treatment agent may be composed solely of the present compound. Here, the present compound is preferably compound (1) wherein $B^1$ is $R^{F1}$—O— or $D^1$-$Q^1$-O—$CH_2$—, or a mixture of compound (1) wherein $B^1$ is $R^{F1}$—O— or $D^1$-$Q^1$-O—$CH_2$— and compound (1) wherein $B^1$ is $A^2$-O—. The present surface treatment agent may contain compounds (hereinafter referred to also as impurities) which are included inevitably in the production of the present compound. The present surface treatment agent may contain other components other than the present compound and impurities.

(Other Components)

Other components may, for example, be a perfluoropolyether compound having no phosphoric acid groups (hereinafter referred to also as a fluorinated ether compound) or a catalyst.

<Fluorinated Ether Compound>

The fluorinated ether compound may, for example, be a compound produced in the production step of compound (1) as a by-product or a known (especially, commercially available) compound to be used in the same application as compound (1). The fluorinated ether compound is preferably the following compound (7) or compound (8).

<<Compound (7)>>

Compound (7) is a fluorinated ether compound represented by the following formula (7).

(7)

wherein $R^{F5}$ and $R^{F6}$ are each independently a $C_{1-6}$ perfluoroalkyl group, p is an integer of from 1 to 6, and n15 is an integer of from 1 to 200, provided that when n15 is at least 2, $(C_pF_{2p}O)_q$ may be one composed of at least two types of $C_pF_{2p}O$ different in p.

The above description relating to $R^{F1}$ including the preferred examples, will be also applied to examples of $R^{F5}$ and $R^{F6}$.

The above description relating to $(C_mF_{2m}O)_{n1}$ including the preferred examples, will be also applied to examples of $(C_pF_{2p}O)_{n15}$. $(C_pF_{2p}O)_{n15}$ is preferably the same as $(C_mF_{2m}O)_{n1}$ in the formula (1) with a view to effectively using the compound produced as a by-product in the production step of compound (1). For example, in a case where compound (1) is a compound having $[(CF_2O)_{n4}(CF_2CF_2O)_{n5}]$, it is particularly preferred that compound (7) is also a compound having $[(CF_2O)_{n4}(CF_2CF_2O)_{n5}]$.

As compound (7), a commercially available product may be used. As a commercial product, FOMBLIN M, FOMBLIN Y, FOMBLIN Z (manufactured by Solvay Solexis K.K.), Krytox (manufactured by DuPont), DEMNUM (manufactured by DAIKIN INDUSTRIES, LTD.) may, for example, be mentioned.

<<Compound (8)>>

Compound (8) is a fluorinated ether compound represented by the following formula (8).

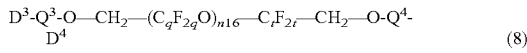
(8)

wherein $D^3$ and $D^4$ are each independently $CF_3$— or $CF_3$—O—, $Q^3$ and $Q^4$ are each independently a $C_{1-20}$ fluoroalkylene group containing at least one hydrogen atom, a $C_{2-20}$ fluoroalkylene group containing at least one hydrogen atom and having an etheric oxygen atom between carbon-carbon atoms, a $C_{1-20}$ alkylene group, or a $C_{2-20}$ alkylene group having an etheric oxygen atom between carbon-carbon atoms, t is an integer of from 1 to 5, q is an integer of from 1 to 6, n16 is an integer of from 1 to 200, provided that when n16 is at least 2, $(C_qF_{2q}O)_{n16}$ may be one composed of at least two types of $(C_qF_{2q}O)$ different in q.

The above description relating to $Q^1$ including the preferred examples, will be also applied to examples of $Q^3$ and $Q^4$. When $Q^3$ and $Q^4$ are a group represented by the formula (6-1), the formula (6-2) or the formula (6-3), $OF^2$ is bonded to $D^3$ in $Q^3$, and $Q^{F2}$ is bonded to $D^4$ in $Q^4$, provided that when $D^3$ is $CF_3$—O—, $Q^{F2}$ is not a single bond in the formula (6-1) and the formula (6-2), and further when $D^4$ is $CF_3$—O—, $Q^{F2}$ is not a single bond in the formula (6-1) or the formula (6-2).

The above description relating to $(C_mF_{2m}O)_{n1}$ including the preferred examples, will be also applied to examples of $(C_qF_{2q}O)_{n16}$. $(C_qF_{2q}O)_{n16}$ is preferably the same as $(C_mF_{2m}O)_{n1}$ in the formula (1) with a view to effectively using the compound (such as compound (3a-2-2)) produced as a by-product in the production step of compound (1). As specific examples of compound (8), the compounds represented by the following formulae are mentioned, wherein the two $Q^{F2}$ groups may be the same or different.

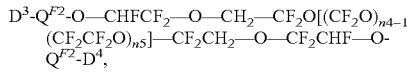

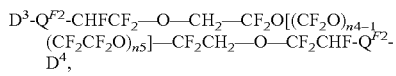

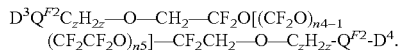

<Catalyst>

The catalyst may, for example, be an acid catalyst or a basic catalyst, which promotes hydrolysis and a condensation reaction of a hydroxy group in the phosphoric acid group of the present compound. The acid catalyst may, for example, be hydrochloric acid, nitric acid, acetic acid, sulfuric acid, phosphoric acid, sulfonic acid, methanesulfonic acid or p-toluenesulfonic acid. The basic catalyst may, for example, be sodium hydroxide, potassium hydroxide or ammonia.

(Composition)

In a case where the present compound in the present surface treatment agent is a mixture of compound (1) wherein $B^1$ is $R^{F1}$—O— or $D^1$-$Q^1$-O—$CH_2$— and compound (1) wherein $B^1$ is $A^2$-O—, the content of compound (1) wherein $B^1$ is $A^2$-O— is preferably from 10 to 60 parts by mass, particularly preferably from 20 to 50 parts by mass, per 100 parts by mass in total of compound (1) wherein $B^1$ is $R^{F1}$-O— or $D^1$-$Q^1$-O—$CH_2$—. When the content of compound (1) wherein $B^1$ is $A^2$-O— is at least the lower limit value of the above range, it is possible to impart excellent abrasion resistance to the substrate surface, and when the content is at most the upper limit value of the above range, it is possible to impart excellent water/oil repellency, fingerprint stain removability and lubricity to the substrate surface.

In the present surface treatment agent, the content of the fluorinated ether compound is preferably at most 30 mass %, particularly preferably at most 20 mass %.

In the present surface treatment agent, the content of the catalyst is preferably at most 10 mass %, particularly preferably at most 1 mass %.

In the present surface treatment agent, the content of other components other than the fluorinated ether compound and the catalyst is preferably at most 10 mass %, particularly preferably at most 1 mass %.

[Coating Liquid]

The coating liquid of the present invention (hereinafter referred to also as the present coating liquid) contains the present surface treatment agent and a liquid medium. The present coating liquid is not particularly limited so long as it is in a liquid form, and it may be a solution or a dispersion.

The solid content concentration in the present coating liquid is preferably from 0.001 to 10 mass %, particularly preferably from 0.01 to 1 mass %. The solid content concentration of the present coating liquid is a value calculated from the mass of the present surface treatment agent before heating and the mass after heating by a convection dryer at 120° C. for 4 hours.

The concentration of the present compound in the present coating liquid is preferably from 0.001 to 10 mass %, particularly preferably from 0.1 to 1 mass %.

(Liquid Medium)

The liquid medium is preferably an organic solvent. The organic solvent may be a fluorinated organic solvent or a non-fluorinated organic solvent, or both solvents may be used in combination. The amount of the liquid medium is preferably from 90 to 99.999 mass %, particularly preferably from 99 to 99.9 mass %, in the present coating liquid.

The fluorinated organic solvent may, for example, be a fluorinated alkane, a fluorinated aromatic compound, a fluoroalkyl ether, a fluorinated alkylamine or a fluoroalcohol, and in view of solubility of the present compound, preferred is a fluorinated alkane, a fluorinated aromatic compound or a fluoroalkyl ether, particularly preferred is a fluoroalkyl ether.

As a fluorinated alkane, a $C_{4-8}$ compound may be mentioned. As a commercial product, $C_6F_{13}H$ (AC-2000: product name, manufactured by Asahi Glass Company, Limited), $C_6F_{13}C_2H_5$ (AC-6000: product name, manufactured by Asahi Glass Company, Limited) or $C_2F_5CHFCHFCF_3$ (Vertrel: product name, manufactured by DuPont) may, for example, be mentioned.

As a fluorinated aromatic compound, hexafluorobenzene, trifluoromethylbenzene, perfluorotoluene or bis(trifluoromethyl)benzene may, for example, be mentioned.

As a fluoroalkyl ether, a $C_{4-12}$ compound may be mentioned. As a commercial product, $CF_3CH_2OCF_2CF_2H$ (AE-3000: product name, manufactured by Asahi Glass Company, Limited), $C_4F_9OCH_3$ (Novec-7100: product name, manufactured by 3M), $C_4F_9OC_2H_5$ (Novec-7200: product name, manufactured by 3M) or $C_6F_{13}OCH_3$ (Novec-7300: product name, manufactured by 3M) may, for example, be mentioned.

As a fluorinated alkylamine, perfluorotripropylamine or perfluorotributylamine may, for example, be mentioned. As a fluoroalcohol, 2,2,3,3-tetrafluoropropanol, 2,2,2-trifluoroethanol or hexafluoroisopropanol may, for example, be mentioned.

The non-fluorinated organic solvent may be a compound composed solely of hydrogen atoms and carbon atoms or a compound composed solely of hydrogen atoms, carbon atoms and oxygen atoms, preferred is a hydrocarbon type organic solvent, an alcohol type organic solvent, a ketone type organic solvent, an ether type organic solvent, or an ester type organic solvent, and in view of solubility of the present compound, particularly preferred is a ketone type organic solvent.

The hydrocarbon type organic solvent is preferably hexane, heptane, cyclohexane or the like.

The alcohol type organic solvent is preferably methanol, ethanol, 1-propanol, 2-propanol or the like.

The ketone type organic solvent is preferably acetone, methyl ethyl ketone, methyl isobutyl ketone or the like.

The ether type organic solvent is preferably diethyl ether, tetrahydrofuran, tetraethylene glycol dimethyl ether or the like.

The ester type organic solvent is preferably ethyl acetate, butyl acetate or the like.

The liquid medium is preferably at least one organic solvent selected from the group consisting of a fluorinated alkane, a fluorinated aromatic compound, a fluoroalkyl ether, a compound composed solely of hydrogen atoms and carbon atoms and a compound composed solely of hydrogen atoms, carbon atoms and oxygen atoms. Particularly preferred is at least one fluorinated organic solvent selected from the group consisting of a fluorinated alkane, a fluorinated aromatic compound and a fluoroalkyl ether.

With a view to improving the solubility of the present compound, the amount of such a solvent is at least 90 mass % based on the entire liquid medium.

[Substrate]

As a material for a substrate, an inorganic material, an organic material or a composite material thereof may be mentioned.

As an inorganic material, glass, a single crystal material, metal, stone or a composite material thereof may, for example, be mentioned, and preferred is glass, a single crystal material or a composite material thereof.

As glass, preferred is soda lime glass, alkali aluminosilicate glass, borosilicate glass, alkali-free glass, crystal glass or quartz glass, and particularly preferred is chemically tempered soda lime glass, chemically tempered alkali aluminosilicate glass or chemically tempered borosilicate glass.

As a single crystal material, preferred is zinc oxide, titanium oxide, diamond, sapphire or the like, and particularly preferred is sapphire. Sapphire is an α-type alumina (hexagonal) single crystal material having a corundum structure. The crystal orientation surface of sapphire may be any of the following.

surface c (0, 0, 0, 1), surface a (1, 1, $\bar{2}$, 0),
surface m (1, $\bar{1}$, 0, 0), surface r (1 $\bar{1}$, 0, 2).

The crystal orientation surface of sapphire is preferably surface a in view of high strength. Further, in order to impart a desired hardness and light transmitting property to the sapphire substrate itself, amorphous alumina, transparent alumina, another sapphire-like material, a polycrystal compound or the like may be combined. As a process for producing sapphire may be a Verneuil method, a Czochralski method or EPG (Edge-defined film-fed Growth) method may be mentioned.

The organic material may, for example, be a resin. The resin is preferably an acrylic resin or a polycarbonate resin.

The material for the substrate is preferably sapphire. When the substrate is a sapphire substrate, the present surface treatment agent can impart more excellent water/oil repellency, fingerprint stain removability, abrasion resistance and lubricity to the sapphire substrate surface. Therefore, the present surface treatment agent is preferably a surface treatment agent for a sapphire substrate.

The substrate is preferably a substrate having a light transmitting property (hereinafter referred to also as a transparent substrate). "A light transmitting property" means that the normal incidence visible transmittance in accordance with JIS R1306 is at least 25%, preferably at least 50%.

(Surface Layer)

The thickness of the surface layer is preferably from 1 to 100 nm, particularly preferably from 1 to 50 nm. When the thickness of the surface layer is at least the lower limit value of the above range, the water/oil repellency and the fingerprint strain removability are excellent. When it is at most the upper limit value of the above range, the cost can be reduced, and further the light transmittance of a sapphire substrate having such a surface layer becomes high.

Further, the thickness of the surface layer can be obtained in such a manner that an X-ray diffractometer ATX-G (manufactured by Rigaku Corporation) for thin-film analysis is used to obtain an interference pattern of reflected X-rays by means of an X-ray reflectance method, and a film thickness is calculated from the oscillation period of the interference pattern.

(Production Process)

A process for producing a substrate having a surface layer has a step of treating the substrate surface by using the present surface treatment agent or coating liquid of the present invention. The treating method may be a dry coating method or an wet coating method.

<Dry Coating Method>

A process for producing a substrate having a surface layer by means of a dry coating method, has a step of dry coating the substrate surface with the surface treatment agent of the present invention.

The dry coating method may, for example, be a technique such as vacuum deposition, CVD or sputtering. With a view to suppressing decomposition of the present compound and in view of simplicity of an apparatus, a vacuum deposition method is preferred. The vacuum deposition method can be classified into a resistance heating method, an electron beam heating method, a high frequency induction heating method, a reactive deposition method, a molecular beam epitaxy method, a hot wall deposition method, an ion plating method, a cluster ion beam method, etc., and any method can be used. A resistance heating method can be suitably used with a view to suppressing decomposition of the present compound and in view of simplicity of an apparatus. A vacuum deposition apparatus is not particularly limited, and a known apparatus may be used.

In a case where a vacuum deposition method is employed, the film deposition conditions vary depending upon the type of the vacuum deposition method to be applied, and in the case of a resistance heating method, the degree of vacuum before deposition is preferably at most $1 \times 10^{-2}$ Pa, particularly preferably at most $1 \times 10^{-3}$ Pa. The heating temperature of the deposition source is preferably from 30 to 400° C., particularly preferably from 50 to 300° C. When the heating temperature is at least the lower limit value of the above range, the film deposition rate will be excellent. When it is at most the upper limit value of the above range, it is possible to impart water/oil repellency, abrasion resistance and fingerprint stain removability to the substrate surface without causing decomposition of the present compound. At the time of vacuum deposition, the substrate temperature is preferably within a range of from room temperature (20 to 25° C.) to 200° C. When the substrate temperature is at most 200° C., the film deposition rate will be excellent. The upper limit value of the substrate temperature is more preferably at most 150° C., particularly preferably at most 100° C.

<Wet Coating Method>

A process for producing a substrate having a surface layer by means of a wet coating method, has a step of coating the substrate surface with the surface treatment agent or coating liquid of the present invention. In the case of using a coating liquid, a step of removing a liquid medium is further included.

The coating method is preferably a spin coating method, a wipe coating method, a spray coating method, a squeegee coating method, a dip coating method, a die coating method, an ink jet method, a flow coating method, a roll coating method, a casting method, a Langmuir-Blodgett method or a gravure coating method.

The method for removing a liquid medium may be heating, vacuuming, and heating and vacuuming. The temperature for drying is preferably from 10 to 300° C., particularly preferably from 20 to 200° C.

<Post Treatment>

After the surface layer is formed on the substrate, an operation to promote the reaction of the present compound with the substrate may be carried out, as the case requires, in order to improve the abrasion resistance on the substrate surface. Such an operation may, for example, be e.g. heating or moisturizing. For example, a substrate having the surface layer formed thereon may be heated in an atmosphere containing moisture, whereby it is possible to promote the reaction such as a reaction of e.g. a hydroxy group present on the substrate surface with a hydroxy group in the phosphoric acid group. After the surface treatment, a compound in the surface-treated layer which is not chemically bonded to another compound or the substrate, may be removed as the case requires. As a specific method, for example, a method of washing the surface-treated layer with a solvent, or a method of wiping the surface-treated layer with cloth impregnated with a solvent, may be mentioned.

EXAMPLES

Now, the present invention will be described in further detail with reference to Examples. However, it should be understood that the present invention is by no means restricted to such specific Examples. In the following, "%" means "mass %" unless otherwise specified. Ex. 1 to 7 are Examples of the present invention, and Ex. 8 is Comparative Example.

[Evaluation Methods]

(Method for Measuring Water Contact Angle and n-Hexadecane Contact Angle)

The contact angle of about 2 µL of distilled water or n-hexadecane placed on the surface of a surface layer of a substrate was measured by a contact angle measuring apparatus DM-500 (manufactured by Kyowa Interface Science Co., Ltd.). Measurement was carried out on different five positions on the surface of a surface layer of a substrate, and their average value was calculated. To calculate the contact angle, 2θ method was employed.

(Abrasion Resistance)

With respect to the substrate having a surface layer, in accordance with JIS L0849, a cellulose nonwoven fabric (product name: BEMCOT M-3, manufactured by Asahi Kasei Corporation) was reciprocated 1,000 times under a load of 1 kg by means of a reciprocal traverse tester (manufactured by KNT), whereupon the water contact angle and the n-hexadecane contact angle were measured.

The smaller the decrease of the water repellency (water contact angle) and the oil repellency (n-hexadecane contact angle) become when the number of abrasion times was increased, the smaller the decrease in the performance by abrasion becomes, and the better the abrasion resistance becomes.

(Fingerprint Stain Removability)

An artificial fingerprint liquid (a liquid composed of oleic acid and squalene) was deposited on a flat surface of a silicon rubber stopper, and then, excess oil was wiped off with a nonwoven fabric (BEMCOT M-3, manufactured by Asahi Kasei Corporation) to prepare a fingerprint stamp. On a surface layer of a substrate having the surface layer, the fingerprint stamp was placed and pressed under a load of 1 kg for 10 seconds so that the fingerprint was attached on the entire surface of the surface layer of the substrate. Then, the fingerprint attached on the surface layer was wiped off under a load of 500 g by means of a reciprocal traverse tester (manufactured by KNT) having tissue paper attached. The haze value was measured after every wiping reciprocation, and if it reached 0.5 or lower within 10 wiping reciprocations, such a case was taken as "acceptable", and if it failed to reach 0.5 or lower, such a case was taken as "not acceptable".

<Dynamic Friction Coefficient>

By means of a variable normal load friction and wear measurement system HHS2000 (manufactured by SHINTO Scientific Co., Ltd.), the dynamic friction coefficient of a substrate having a surface layer against an artificial skin (PBZ13001, manufactured by Idemitsu Technofine) was measured under conditions of a contact area of 3 cm×3 cm and a load of 100 g.

The smaller the dynamic friction coefficient, the better the lubricity.

Ex. 1: Production of Compound (1a-1-1)

Ex. 1-1

Into a 300 mL three-necked round-bottomed flask, 14.1 g of a sodium borohydride powder was put, and 350 g of ASAHIKLIN (tradename) AK-225 (product name of a mixture of 48 mol % of HCFC-225ca and 52 mol % of HCFC-225cb, manufactured by Asahi Glass Company, Limited, hereinafter, referred to also as "AK-225") was added. While cooling and stirring in an ice bath, a solution having 100 g of compound (12a), 15.8 g of methanol and 22 g of AK-225 mixed, was slowly dropwise added from a dropping funnel in a nitrogen atmosphere so that the internal temperature would not exceed 10° C. After dropwise addition of the entire amount, a solution having 10 g of methanol and 10 g of AK-225 mixed, was dropwise added. Then, the ice bath was removed, and while raising the temperature slowly to room temperature, stirring was continued. After stirring at room temperature for 12 hours, the reaction mixture was cooled again in an ice bath, and an aqueous hydrochloric acid solution was dropwise added until the liquid became acidic. After termination of the reaction, the reaction mixture was washed once with water and once with a saturated aqueous sodium chloride solution, whereupon an organic phase was recovered. The recovered organic phase was dried over magnesium sulfate, and then, the solid content was filtered off, and the filtrate was concentrated by an evaporator. The recovered concentrated liquid was distilled under reduced pressure to obtain 80.6 g (yield: 88%) of compound (11a).

$$CF_2=CFO-CF_2CF_2CF_2C(=O)OCH_3 \quad (12a)$$

$$CF_2=CFO-CF_2CF_2CF_2CH_2OH \quad (11a)$$

NMR spectrum of compound (11a):
$^1$H-NMR (300.4 MHz, solvent: deuterated chloroform, standard: TMS) δ (ppm): 2.2 (1H), 4.1 (2H).
$^{19}$F-NMR (282.7 MHz, solvent: deuterated chloroform, standard: CFCl$_3$) δ (ppm): −85.6 (2F), −114.0 (1F), −122.2 (1F), −123.3 (2F), −127.4 (2F), −135.2 (1F).

Ex. 1-2

Into a 50 mL eggplant flask connected to a reflux condenser, 5.01 g of compound (11a) obtained in Ex. 1-1 and 5.06 g of methanol were put, and 0.54 g of potassium hydroxide pellets were added. After stirring at 25° C. all-night in a nitrogen atmosphere, excess potassium hydroxide was treated by adding an aqueous hydrochloric acid solution, and water and AK-225 were added to carry out liquid separation treatment. After washing with water three times, the organic phase was recovered and concentrated by an evaporator to obtain 5.14 g of a methanol adduct. Into a 50 mL eggplant flask connected to a reflux condenser, 1.0 g of the methanol adduct and 0.13 g of potassium hydroxide pellets were added again, and 10.86 g of compound (11a) was dropwise added while heating to 100° C. Stirring was further carried out for 9 hours while maintaining 100° C., excess potassium hydroxide was treated by adding an aqueous hydrochloric acid solution, and water and AK-225 were added to carry out liquid separation treatment. After washing three times with water, the organic phase was recovered and concentrated by an evaporator to obtain 11 g of an oligomer with a high viscosity. It was diluted again with AK-225 to two times, and developed and fractionated by silica gel column chromatography (developing solvent: AK-225).

With respect to each fraction, an average value of unit number (n+1) was obtained from the integrated value of $^{19}$F-NMR. 4.76 g of compound (10a-1) having fractions with an average value of (n6+1) being from 7 to 10 in the following formula (10a-1) put together, was obtained.

$$CH_3-O-(CF_2CFHO-CF_2CF_2CF_2CH_2O)_{n6+1}-H \qquad (10a-1)$$

NMR Spectrum of Compound (10a-1):

$^1$H-NMR (300.4 MHz, solvent: deuterated chloroform, standard: TMS) δ (ppm): 3.7 (3H), 4.0 (2H), 4.4 (18.4H), 6.0 to 6.2 (9.2H).

$^{19}$F-NMR (282.7 MHz, solvent: deuterated chloroform, standard: CFCl$_3$) δ (ppm): −84.7 to −87.0 (18.4F), −89.4 to −91.6 (18.4F), −121.5 (16.4F), −123.4 (2F), −128.0 (18.4F), −145.3 (9.2F).

Average value of unit number (n6+1): 9.2

Ex. 1-3

Into a 200 mL eggplant flask connected to a reflux condenser, 100 g of compound (10a-1) obtained in Ex. 1-2 was put, and 28.6 g of acetyl chloride was dropwise added thereto over 20 minutes with stirring at room temperature in a nitrogen atmosphere. Stirring was carried out at 50° C. for 4.5 hours, whereupon disappearance of raw materials was confirmed by means of $^1$H-NMR. The reaction solution was concentrated by an evaporator. The solution after the concentration was diluted with AK-225 and treated with 20 g of silica gel, and then a solid content was removed by filtration. The solution was concentrated again by an evaporator to obtain 98.1 g (yield: 97%) of compound (9a-1) having an average value of unit number (n6+1) being 9.2, in the following formula (9a-1).

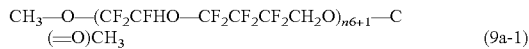

$$CH_3-O-(CF_2CFHO-CF_2CF_2CF_2CH_2O)_{n6+1}-C(=O)CH_3 \qquad (9a-1)$$

NMR Spectrum of Compound (9a-1):

$^1$H-NMR (300.4 MHz, solvent: deuterated chloroform+R-113 (CCl$_2$FCClF$_2$), standard: TMS) δ (ppm): 2.0 (3H), 3.6 (3H), 4.4 to 4.9 (18.4H), 6.0 to 6.2 (9.2H).

$^{19}$F-NMR (282.7 MHz, solvent: deuterated chloroform+R-113, standard: CFCl$_3$) (ppm): −85.5 to −86.7 (18.4F), −91.5 to −93.9 (18.4F), −121.7 to −122.8 (18.4F), −128.4 to −129.6 (18.4F), −145.9 (9.2F).

Average value of unit number (n6+1): 9.2

Ex. 1-4

An autoclave (made of nickel, internal capacity: 1 L) was provided, and at a gas discharge outlet of the autoclave, a condenser held at 25° C., a NaF pellets-packed layer and a condenser held at 0° C. were set in series. Further, a liquid-returning line to return a liquid condensed from the condenser held at 0° C. to the autoclave, was set.

Into the autoclave, 750 g of R-419 (CF$_2$ClCFClCF$_2$OCF$_2$CF$_2$Cl) was put and stirred while maintaining the temperature at 25° C. After blowing nitrogen gas at 25° C. for one hour into the autoclave, fluorine gas diluted to 20 vol % with nitrogen gas (hereinafter referred to as the 20% fluorine gas), was blown at 25° C. for one hour at a flow rate of 5.3 L/hr. Then, while blowing the 20% fluorine gas at the same flow rate, a solution having 70 g of compound (9a-1) obtained in Ex. 1-3 dissolved in 136 g of R-419, was injected into the autoclave over a period of 7.4 hours.

Then, while blowing the 20% fluorine gas at the same flow rate, the internal pressure of the autoclave was raised to 0.15 MPa (gauge pressure). Into the autoclave, 4 mL of a benzene solution containing 0.0056 g/mL of benzene in R-419, was injected while heating from 25° C. to 40° C., whereupon the benzene solution injection inlet of the autoclave was closed. After stirring for 20 minutes, 4 mL of the benzene solution was injected again while maintaining the temperature at 40° C., whereupon the injection inlet was closed. The same operation was further repeated 4 times. The total injected amount of benzene was 0.1 g.

Further, stirring was continued for one hour while blowing the 20% fluorine gas at the same flow rate. Then, the internal pressure of the autoclave was adjusted to the atmospheric pressure, and nitrogen gas was injected for one hour. The content in the autoclave was concentrated by an evaporator to obtain 82.3 g (yield: 97%) of compound (7a-1) having an average value of unit number (n6) being 8.2 in the following formula (7a-1).

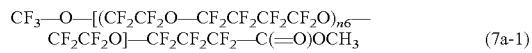

$$CF_3-O-[(CF_2CF_2O-CF_2CF_2CF_2CF_2O)_{n6}-CF_2CF_2O]-CF_2CF_2CF_2-C(=O)OCH_3 \qquad (7a-1)$$

NMR Spectrum of Compound (7a-1):

$^{19}$F-NMR (282.7 MHz, solvent: deuterated chloroform+R-113, standard: CFCl$_3$) δ (ppm): −57.3 (3F), −77.5 (3F), −85.0 (34.8F), −88.5 (2F), −90.5 (34.8F), −92.5 (2F), −127.5 (36.8).

Average value of unit number (n6): 8.2

Ex. 1-5

Into a 500 mL round-bottomed eggplant flask made of a tetrafluoroethylene-perfluoro(alkoxyvinyl ether) copolymer (PFA), 82.3 g of compound (7a-1) obtained in Ex. 1-4 and 250 mL of AK-225 were put. 3.9 g of methanol was slowly dropwise added from a dropping funnel, in a nitrogen atmosphere, followed by stirring for 12 hours. The reaction mixture was concentrated by an evaporator to obtain 77.7 g (yield: 100%) of compound (6a-1) having an average value of unit number (n6) being 8.2 in the following formula (6a-1).

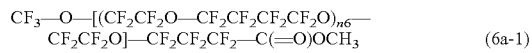

$$CF_3-O-[(CF_2CF_2O-CF_2CF_2CF_2CF_2O)_{n6}-CF_2CF_2O]-CF_2CF_2CF_2-C(=O)OCH_3 \qquad (6a-1)$$

NMR Spectrum of Compound (6a-1):

$^1$H-NMR (300.4 MHz, solvent: deuterated chloroform+R-113, standard: TMS) δ (ppm): 3.8 (3H).

$^{19}$F-NMR (282.7 MHz, solvent: deuterated chloroform+R-113, standard: CFCl$_3$) δ (ppm): −57.3 (3F), −84.9 (34.8F), −90.5 (34.8F), −92.5 (2F), −120.2 (2F), −127.3 (32.8F), 128.2 (2F).

Average value of unit number (n6): 8.2

Ex. 1-6

Into a 100 mL round-bottomed eggplant flask, 33.5 g of compound (6a-1) obtained in Ex. 1-5 and 0.59 g of H$_2$NCH$_2$CH$_2$OH were put, followed by stirring at room temperature for 9 hours. The resulting reaction product was concentrated by an evaporator to obtain 33.8 g (yield: 100%) of compound (5a-1) having an average value of unit number (n6) being 8.2 in the following formula (5a-1).

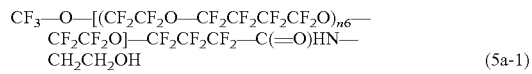

$$CF_3-O-[(CF_2CF_2O-CF_2CF_2CF_2CF_2O)_{n6}-CF_2CF_2O]-CF_2CF_2CF_2-C(=O)HN-CH_2CH_2OH \qquad (5a-1)$$

NMR Spectrum of Compound (5a-1):

$^1$H-NMR (300.4 MHz, solvent: deuterated chloroform+R-113, standard: TMS) δ (ppm): 2.7 (2H), 3.5 (2H).

$^{19}$F-NMR (282.7 MHz, solvent: deuterated chloroform +R-113, standard: CFCl$_3$) δ (ppm): −57.3 (3F), −84.9 (34.8F), −90.5 (34.8F), −92.5 (2F), −120.2 (2F), −127.3 (32.8F), 128.2 (2F).

Average value of unit number (n6): 8.2

Ex. 1-7

Into a 100 mL round-bottomed eggplant flask, 33.8 g of compound (5a-1) obtained in Ex. 1-6 and 1.51 g of phosphorus oxychloride were put, followed by stirring at room temperature for 9 hours. 2.0 g of water was added to the resulting solution, followed by stirring at room temperature for 30 minutes. The resulting reaction product was concentrated by an evaporator to obtain 34.6 g (yield: 100%) of compound (1a-1-1) having an average value of unit number (n6) being 8.2 in the following formula (1a-1). The number average molecular weight of compound (1a-1-1) is 3,600.

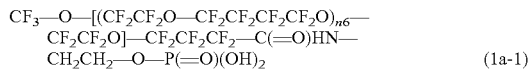  (1a-1)

NMR Spectrum of Compound (1a-1-1):

$^1$H-NMR (300.4 MHz, solvent: deuterated chloroform+R-113, standard: TMS) δ (ppm): 2.8 (2H), 3.4 (2H).

$^{19}$F-NMR (282.7 MHz, solvent: deuterated chloroform+R-113, standard: CFCl$_3$) δ (ppm): −57.3 (3F), −84.9 (34.8F), −90.5 (34.8F), −92.5 (2F), −120.2 (2F), −127.3 (32.8F), 128.2 (2F)

Average value of unit number (n6): 8.2

Ex. 2: Production of Compound (1a-2-1)

Ex. 2-1

Into a 500 mL three-necked round-bottomed flask, 1.04 g of potassium hydroxide was put, and 83 g of tert-butanol and 125 g of 1,3-dis(trifluoromethyl)benzene were added. The potassium hydroxide was dissolved by stirring at room temperature, and 250 g of compound (4a-2) (FLUOROLINK D10/H: product name, manufactured by Solvay Solexis K.K.) was added thereto, followed by stirring for one hour. At room temperature, 38.2 g of perfluoro(propyl vinyl ether) (CF$_3$CF$_2$CF$_2$—O—CF=CF$_2$) was added, followed by stirring for further 24 hours. Hydrochloric acid was added for neutralization, and water was further added for liquid separation treatment. After washing three times with water, the organic phase was recovered and concentrated by an evaporator to obtain 288.0 g of a reaction crude liquid. It was again diluted with 144 g of AC-2000 and developed and fractionated by silica gel column chromatography (developing solvent: AC-2000 and AE-3000), whereby 136.2 g (yield: 47%) of compound (3a-2) was obtained.

  (3a-2)

NMR Spectrum of Compound (3a-2):

$^1$H-NMR (300.4 MHz, solvent: deuterated acetone+R-113, standard: TMS) δ (ppm): 3.9 (2H), 4.6 (2H), 5.1 (1H), 6.3 (1H).

$^{19}$F-NMR (282.7 MHz, solvent: deuterated acetone+R-113, standard: CFCl$_3$) δ (ppm): −52.3 to −54.2 (11.2F), −77.7 to −88.2 (9F), −89.4 to −91.1 (38.4F), −130.5 (2F), −145.2 (1F).

Average value of unit number (n7): 6.6
Average value of unit number (n8): 9.6

Ex. 2-2

Into a 50 mL two-necked round-bottomed flask, 391 mg of cesium carbonate, 1.50 g of compound (3a-2) and 106 mg of ethylene carbonate were added, and heated and stirred at 160° C. for 36 hours. To the obtained solution, 15 g of AK-225 and 10 g of dilute hydrochloric acid were added. The organic layer and the aqueous layer were separated, and the organic layer was washed three times with 30 mL of ion-exchanged water and dehydrated with sodium sulfate, followed by distilling off the solvent under reduced pressure to obtain 1.07 g (yield: 70%) of compound (2a-2).

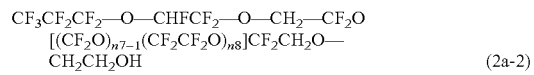  (2a-2)

NMR Spectrum of Compound (2a-2):

$^1$H-NMR (300.4 MHz, solvent: deuterated acetone+R-113, standard: TMS) δ (ppm): 3.69 (4H), 4.04 (2H), 4.64 (2H), 6.40 to 6.83 (1H).

$^{19}$F-NMR (282.7 MHz, solvent: deuterated acetone+R-113, standard:CFCl$_3$) δ (ppm): −52.3 to −54.2 (11.2F), −77.7 to −88.2 (9F), −89.4 to −91.1 (38.4F), −130.5 (2F), −145.2 (1F).

Average value of unit number (n7): 6.6
Average value of unit number (n8): 9.6

Ex. 2-3

Into a 50 mL round-bottomed eggplant flask, 1.0 g of compound (2a-2) obtained in Ex. 2-2 and 65.9 mg of phosphorus oxychloride were added, followed by stirring at room temperature for 9 hours. 2.0 g of water was added to the resulting solution, followed by stirring at room temperature for 30 minutes. The resulting reaction product was concentrated by an evaporator to obtain 1.0 g (yield: 100%) of compound (1a-2-1). The number average molecular weight of compound (1a-2-1) is 2,400.

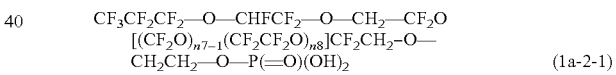  (1a-2-1)

NMR Spectrum of Compound (1a-2-1):

$^1$H-NMR (300.4 MHz, solvent: deuterated acetone+R-113, standard: TMS) δ (ppm): 3.69 (2H), 4.04 (2H), 4.32 (2H), 4.64 (2H), 6.40 to 6.83 (1H).

$^{19}$F-NMR (282.7 MHz, solvent: deuterated acetone+R-113, standard: CFCl$_3$) δ (ppm): −52.3 to −54.2 (11.2F), −77.7 to −88.2 (9F), −89.4 to −91.1 (38.4F), −130.5 (2F), −145.2 (1F).

Ex. 3: Production of Compound (1a-3)

Ex. 3-1

In accordance with a method described in Ex. 1 of JP-A-2011-116947, a mixture of compounds (3a-3), (3a-3-2) and (4a-3) was obtained.

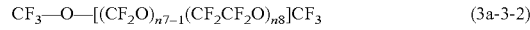  (3a-3-2)

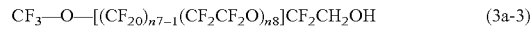  (3a-3)

  (4a-3)

Average value of unit number (n7): 24
Average value of unit number (n8): 21

Ex. 3-2

200 g of the mixture obtained in Ex. (3-1) was diluted with 200 g of AC-2000, and developed and fractionated by silica gel column chromatography (developing solvent: AC-2000 and AE-3000), whereby 90 g (yield: 45%) of compound (3a-3) was obtained. NMR spectrum of compound (3a-3):

$^1$H-NMR (300.4 MHz, solvent: deuterated acetone+R-113, standard: TMS) δ (ppm): 3.9 (2H).

$^{19}$F-NMR (282.7 MHz, solvent: deuterated acetone+R-113, standard: CFCl$_3$) δ (ppm): −52.3 to −54.2 (46F), −54.3 to −56.2 (3F) −78.8 to −81.8 (2F), −89.4 to −91.1 (84F)

Ex. 3-3

Into a 50 mL two-necked round-bottomed flask, 1.0 g of cesium carbonate, 10 g of compound (3a-3) and 162 mg of ethylene carbonate were added, and heated and stirred at 160° C. for 36 hours. To the obtained solution, 50 g of AK-225 and 10 g of dilute hydrochloric acid were added. The organic layer and the aqueous layer were separated, and the organic layer was washed three times with 30 mL of ion-exchanged water and dehydrated with sodium sulfate, followed by distilling off the solvent under reduced pressure to obtain 6.58 g (yield: 65%) of compound (2a-3).

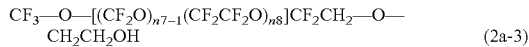

CF$_3$—O—[(CF$_2$O)$_{n7-1}$(CF$_2$CF$_2$O)$_{n8}$]CF$_2$CH$_2$—O—CH$_2$CH$_2$OH     (2a-3)

Average value of unit number (n7): 24
Average value of unit number (n8): 21
NMR Spectrum of Compound (2a-3):

$^1$H-NMR (300.4 MHz, solvent: deuterated acetone+R-113, standard: TMS) δ (ppm): 3.69 (2H), 4.04 (2H), 4.64 (2H).

$^{19}$F-NMR (282.7 MHz, solvent: deuterated acetone+R-113, standard:CFCl$_3$) δ (ppm): −52.3 to −54.2 (46F), −54.3 to −56.2 (3F) −78.8 to −81.8 (2F), −89.4 to −91.1 (84F).

Ex. 3-4

Into a 50 mL round-bottomed flask, 1.0 g of compound (2a-3) obtained in Ex. 3-3 and 30 mg of phosphorus oxychloride were added, and stirred at room temperature for 9 hours. To the obtained solution, 2.0 g of water was added, followed by stirring at room temperature for 30 minutes. The resulting reaction product was concentrated by an evaporator to obtain 1.0 g (yield: 100%) of compound (1a-3). The number average molecular weight of compound (1a-3) was 5,600.

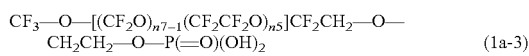

CF$_3$—O—[(CF$_2$O)$_{n7-1}$(CF$_2$CF$_2$O)$_{n5}$]CF$_2$CH$_2$—O—CH$_2$CH$_2$—O—P(=O)(OH)$_2$     (1a-3)

Average value of unit number (n7): 24
Average value of unit number (n8): 21

NMR spectrum of compound (1a-3):

$^1$H-NMR (300.4 MHz, solvent: deuterated acetone+R-113, standard: TMS) δ (ppm): 3.69 (2H), 3.84 (2H), 4.64 (2H).

$^{19}$F-NMR (282.7 MHz, solvent: deuterated acetone+R-113, standard: CFCl$_3$) δ (ppm): −52.3 to −54.2 (46F), −54.3 to −56.2 (3F) −78.8 to −81.8 (2F), −89.4 to −91.1 (84F).

Ex. 4 to 8: Production and Evaluation of Substrate Having Surface Layer

Ex. 4 to 7

<Preparation of Coating Liquid and Wet Coating Method>

The compound obtained in each of Ex. 1 to 3 and C$_4$F$_9$OC$_2$H$_5$ (Novec-7200, product name, manufactured by 3M) as a liquid medium were mixed to prepare a coating liquid having a solid content concentration of 0.05%. A substrate was dipped in the coating liquid (dip coating method), left to stand for 30 minutes and then pulled out. The substrate was dried at 200° C. for 30 minutes and washed with AK-225 which is a fluorinated solvent, to obtain a substrate having a surface layer. The thickness of the surface layer was 10 nm. As the substrate, artificial sapphire (crystal orientation surface: surface c, manufactured by Shinkosha, Co., Ltd.) or chemically tempered glass (alkali aminosilicate glass, manufactured by Asahi Glass Company, Limited) was used.

The evaluation results of water contact angle, n-hexadecane contact angle, abrasion resistance, fingerprint stain removability and dynamic friction coefficient of the surface layer are shown in Table 1.

Ex. 8

<Preparation of Coating Liquid and Wet Coating Method>

Compound (1a-4) represented by the following formula (1a-4) described in Non-Patent Document J. Phys. Chem. C, 2007, 111, 3956-3962, and C$_4$F$_9$OC$_2$H$_5$ (Novec-7200, product name, manufactured by 3M) as a liquid medium, were mixed to prepare a coating liquid having a solid content concentration of 0.05%. A substrate was dipped in the coating liquid (dip coating method), left to stand for 30 minutes and then pulled out. The substrate was dried at 200° C. for 30 minutes and washed with AK-225 to obtain a substrate having a surface layer. The thickness of the surface layer was 10 nm. As the substrate, artificial sapphire (crystal orientation surface: surface c, manufactured by Shinkosha, Co., Ltd.) was used.

The evaluation results of water contact angel, n-hexadecane contact angle, abrasion resistance, fingerprint stain removability and dynamic friction coefficient of the surface layer are shown in Table 1.

CF$_3$(CF$_2$)$_7$CH$_2$CH$_2$P(=O)(OH)$_2$     (1a-4)

TABLE 1

|  |  | Ex. 4 | Ex. 5 | Ex. 6 | Ex. 7 | Ex. 8 |
| --- | --- | --- | --- | --- | --- | --- |
|  | Compound | (1a-1-1) | (1a-2-1) | (1a-3) | (1a-3) | (1a-4) |
|  | Substrate | Artificial sapphire | Artificial sapphire | Artificial sapphire | Glass | Artificial sapphire |
| Water contact angle (°) | Initial | 115 | 113 | 113 | 111 | 108 |
|  | After 1,000 times of abrasion | 114 | 112 | 112 | 110 | 97 |
| n-Hexadecane contact angle (°) | Initial | 65 | 64 | 64 | 64 | 50 |
|  | After 1,000 times of abrasion | 64 | 64 | 63 | 60 | 37 |
| Fingerprint stain removability |  | Acceptable | Acceptable | Acceptable | Acceptable | Not Acceptable |
| Dynamic friction coefficient |  | 0.40 | 0.32 | 0.35 | 0.35 | 0.60 |

From the results in Table 1, water/oil repellency, fingerprint stain removability and lubricity were excellent in Ex. 4 to 7 wherein the present compound was used. Further, in Ex. 4 to 7, the deterioration of water/oil repellency was small or hardly observed, and abrasion resistance was excellent, even when abrasion was repeated 1,000 times to the substrate having the surface layer. On the other hand, water/oil repellency, fingerprint stain removability and lubricity were poor in Ex. 8 wherein compound (1a-4) having no perfluoropolyether group was used. Further, in Ex. 8, water/oil repellency was significantly deteriorated, and abrasion resistance was poor when abrasion was repeated 1,000 times to the substrate having the surface layer.

Further, according to comparison of Ex. 4 to 6, in Ex. 4 wherein compound (1a-1-1) was used, water/oil repellency and abrasion resistance were more improved as compared with Ex. 6 wherein compound (1a-3) was used, and further, in Ex. 5 wherein compound (1a-2-1) was used, abrasion resistance and lubricity were more improved as compared with Ex. 6 wherein compound (1a-3) was used.

INDUSTRIAL APPLICABILITY

A substrate having a surface layer formed by using the present surface treatment agent can be used for electronic materials or optical materials (such as an endoscope lens, a mobile communication device, a fingerprint reader, an automatic remitting machine, a goggle, a camera, an infrared imaging system, a lens, a touch panel or a window), or building materials (such as a flooring material or a wall material). When the substrate is a transparent substrate, the substrate having a surface layer is preferably used for electronic materials or optical materials, particularly preferably used for a member to constitute a touch panel. The touch panel is an input device of an input/display apparatus (touch panel apparatus) having a display device combined with the input device for inputting a contact position information upon touching with e.g. a finger. The touch panel is constituted by a transparent substrate and, depending upon the input detection system, a transparent conductive film, electrodes, a wiring, IC, etc. By using the surface having a surface layer of a transparent substrate as the input surface of a touch panel, it is possible to obtain a touch panel having excellent finger print stain removability and lubricity. When the lubricity is excellent, the touch feeling of the touch panel will be excellent, and the operation efficiency will be improve.

This application is a continuation of PCT Application No. PCT/JP2015/075736, filed on Sep. 10, 2015, which is based upon and claims the benefit of priority from Japanese Patent Application No. 2014-188789 filed on Sep. 17, 2014. The contents of those applications are incorporated herein by reference in their entireties.

What is claimed is:

1. A surface treatment agent, comprising a perfluoropolyether group-containing phosphate compound,
wherein the perfluoropolyether group-containing phosphate compound is a compound represented by formula (1):

$$B^1—(C_mF_{2m}O)_{n1}-A^1 \quad (1)$$

wherein $A^1$ is a monovalent organic group having at least one phosphoric acid group at its terminal, $B^1$ is $R^{F1}$—O— or $D^1$-$Q^1$-O—$CH_2$— and a compound represented by the formula (1) wherein $A^1$ is a monovalent organic group having at least one phosphoric acid group at its terminal, $B^1$ is $A^2$-O—, wherein a content of the compound represented by the formula (1) wherein $B^1$ is $A^2$-O— is from 10 to 60 parts by mass, per 100 parts by mass in total of the compound represented by the formula (1) wherein $B^1$ is $R^{F1}$—O— or $D^1$-$Q^1$-O—$CH_2$, wherein $R^{F1}$ is a $C_{1-6}$ perfluoroalkyl group, $B^1$ is $CF_3$— or $CF_3$—O—, $Q^1$ is a $C_{1-20}$ fluoroalkylene group comprising a hydrogen atom, a $C_{2-20}$ fluoroalkylene group comprising a hydrogen atom and having an etheric oxygen atom between carbon-carbon atoms, a $C_{1-20}$ alkylene group, or a $C_{2-20}$ alkylene group having an etheric oxygen atom between carbon-carbon atoms, and $A^2$ is a monovalent organic group having at least one phosphoric acid group at its terminal, m is an integer of from 1 to 6, and n1 is an integer of from 2 to 200, and wherein $(C_mF_{2m}O)_{n1}$ is a group represented by formula (2-1):

$$(C_rF_{2r}O)_{n2}(C_sF_{2s}O)_{n3} \quad (2-1)$$

wherein r is an integer of from 1 to 3, s is an integer of from 4 to 6, n2 is an integer of at least 1, n3 is an integer of at least 1, provided that n2+n3 is an integer of from 2 to 200, and a bonding order of $(C_rF_{2r}O)$ and $(C_sF_{2s}O)$ is not limited.

2. The surface treatment agent according to claim 1, wherein $A^1$ is a group represented by formula (3):

$$-Q^{F1}(CX_2)_{w1}-E^1-Y^1—O—P(=O)(OH)_2 \quad (3)$$

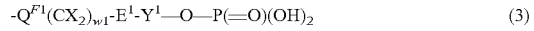

wherein $Q^{F1}$ is a $C_{1-20}$ perfluoroalkylene group, $CX_2$ is $CH_2$ or CHF, w1 is 0 or 1, $E^1$ is a single bond, —C(=O)NH— (provided that $Y^1$ is bonded to N), —OC(=O)NH— (provided that $Y^1$ is bonded to N), —O—, —C(=O)O— (provided that $Y^1$ is bonded to O), —OC(=O)O—, —NHC(=O)NH— or —NHC(=O)O— (provided that $Y^1$ is bonded to O), wherein $Y^1$ is an alkylene group, a poly(oxyalkylene)-alkylene group, a cycloalkylene group, an arylene group, or an alkylene group in which at least one of hydrogen atoms is substituted by a hydroxy group, provided that $E^1$ is not —O—, —OC(=O)NH— or —OC(=O)O-when w1 is 0, and $Y^1$ is not an alkylene group when w1 is 1, $CX_2$ is $CH_2$ and $E^1$ is a single bond.

3. The surface treatment agent according to claim 1, wherein $Q^1$ is a group represented by formula (4-1), (4-2) or (4-3):

$$-Q^{F2}-O—CHFCF_2— \quad (4-1)$$

$$-QF^2—CHFCF_2— \quad (4-2)$$

$$-Q^{F2}-C_zH_{2z}— \quad (4-3)$$

wherein $Q^{F2}$ is a single bond, a $C_{1-15}$ perfluoroalkylene group, or a $C_{2-15}$ perfluoroalkylene group having an etheric oxygen atom between carbon-carbon atoms, $Q^{F2}$ is bonded to $D^1$, and z is an integer of from 1 to 4, provided that $Q^{F2}$ is not a single bond in the formula (4-1) and (4-2) when $D^1$ is $CF_3$—O—.

4. The surface treatment agent according to claim 1, wherein a number average molecular weight (Mn) of the compound represented by the formula (1) is 2,000 to 10,000.

5. The surface treatment agent according to claim 1, wherein in the compound represented by the formula (1), $B^1$ is $R^{F1}$—O— or $D^1$-$Q^1$-O—$CH_2$—.

6. The surface treatment agent according to claim 1, which is suitable for treating a surface of a sapphire substrate.

7. A coating agent comprising the surface treatment agent of claim 1 and a liquid medium.

8. A substrate having a surface layer formed from the surface treatment agent of claim 1.

9. A mixture of a compound represented by formula (1):

$$B^1\text{---}(C_mF_{2m}O)_{n1}\text{-}A^1 \tag{1}$$

wherein $A^1$ is a monovalent organic group having at least one phosphoric acid group at its terminal, $B^1$ is $R^{F1}$—O— or $D^1$-$Q^1$-O—$CH_2$— and a compound represented by the formula (1) wherein $A^1$ is a monovalent organic group having at least one phosphoric acid group at its terminal, $B^1$ is $A^2$-O—, wherein a content of the compound represented by the formula (1) wherein $B^1$ is $A^2$-O— is from 10 to 60 parts by mass, per 100 parts by mass in total of the compound represented by the formula (1) wherein $B^1$ is $R^{F1}$—O— or $D^1$-$Q^1$-O—$CH_2$—, wherein $R^{F1}$ is a $C_{1-6}$ perfluoroalkyl group, $B^1$ is $CF_3$— or $CF_3$—O—, $Q^1$ is a $C_{1-20}$ fluoroalkylene group comprising a hydrogen atom, a $C_{2-20}$ fluoroalkylene group comprising a hydrogen atom and having an etheric oxygen atom between carbon-carbon atoms, a $C_{1-20}$ alkylene group, or a $C_{2-20}$ alkylene group having an etheric oxygen atom between carbon-carbon atoms, $A^2$ is a monovalent organic group having at least one phosphoric acid group at its terminal, m is an integer of from 1 to 6, and n1 is an integer of from 2 to 200, and wherein $(C_mF_{2m}O)_{n1}$ is a group represented by formula (2-1):

$$(C_rF_{2r}O)_{n2}(C_sF_{2s}O)_{n3} \tag{2-1}$$

wherein r is an integer of from 1 to 3, s is an integer of from 4 to 6, n2 is an integer of at least 1, n3 is an integer of at least 1, provided that n2+n3 is an integer of from 2 to 200, and a bonding order of $(C_rF_{2r}O)$ and $(C_sF_{2s}O)$ is not limited.

* * * * *